(12) United States Patent
Parthasaradhi Reddy et al.

(10) Patent No.: US 8,471,012 B2
(45) Date of Patent: Jun. 25, 2013

(54) HYDRATED FORM OF ERLOTINIB FREE BASE AND A PROCESS FOR PREPARATION OF ERLOTINIB HYDROCHLORIDE POLYMORPH FORM A SUBSTANTIALLY FREE OF POLYMORPH FORM B

(75) Inventors: Bandi Parthasaradhi Reddy, Andra Pradesh (IN); Kura Rathnakar Reddy, Hyderabad (IN); Rapolu Raji Reddy, Hyderabad (IN); Dasari Muralidhara Reddy, Hyderabad (IN); Thungathurthy Srinivas Rao, Andhra Pradesh (IN)

(73) Assignee: Hetero Drugs Limited (IN)

( * ) Notice: Subject to any disclaimer, the term of this patent is extended or adjusted under 35 U.S.C. 154(b) by 0 days.

(21) Appl. No.: 13/221,986

(22) Filed: Aug. 31, 2011

(65) Prior Publication Data

US 2012/0022256 A1    Jan. 26, 2012

Related U.S. Application Data

(62) Division of application No. 11/994,599, filed as application No. PCT/IN2007/000351 on Aug. 17, 2007, now abandoned.

(51) Int. Cl.
*C07D 239/94*    (2006.01)

(52) U.S. Cl.
USPC .......................................................... 544/293

(58) Field of Classification Search
USPC .......................................................... 544/293
See application file for complete search history.

(56) References Cited

U.S. PATENT DOCUMENTS

| 5,747,498 | A | 5/1998 | Schnur et al. |
| 2004/0162300 | A1 | 8/2004 | Bubendorf et al. |
| 2006/0154941 | A1 | 7/2006 | Huang |
| 2008/0058355 | A1* | 3/2008 | Westheim .................. 514/266.4 |

FOREIGN PATENT DOCUMENTS

| WO | 99/55683 A1 | 11/1999 |
| WO | 0134574 A1 | 3/2001 |

* cited by examiner

*Primary Examiner* — Brian McDowell
(74) *Attorney, Agent, or Firm* — Cantor Colburn LLP

(57) ABSTRACT

The present invention provides a novel and stable hydrated form of erlotinib free base, and a process for its preparation thereof. The present invention also provides a process for preparation of erlotinib hydrochloride crystalline polymorph a substantially free of polymorph B. The present invention further relates to erlotinib hydrochloride crystalline particles having mean particle size ($D_{50}$) ranging from about 4 μm to 15 μm and 90 volume-% of the particles ($D_{90}$) ranging from about 14 μm to 30 μm, to the methods for the manufacture of said crystalline particles, and to pharmaceutical compositions comprising said crystalline particles.

7 Claims, 5 Drawing Sheets

DSC

DSC

HYDRATED FORM OF ERLOTINIB FREE BASE AND A PROCESS FOR PREPARATION OF ERLOTINIB HYDROCHLORIDE POLYMORPH FORM A SUBSTANTIALLY FREE OF POLYMORPH B

CROSS-REFERENCE TO RELATED APPLICATIONS

This application claims the benefit of U.S. patent application Ser. No. 11/994,599, filed Jan. 3, 2008, which claims priority to PCT/IN07/00351 filed Aug. 17, 2007, all of which are incorporated by reference herein in their entirety.

FIELD OF THE INVENTION

The present invention provides a novel and stable hydrated form of erlotinib free base, and a process for its preparation thereof. The present invention also provides a process for preparation of erlotinib hydrochloride crystalline polymorph A substantially free of polymorph B. The present invention further relates to erlotinib hydrochloride crystalline particles having mean particle size ($D_{50}$) ranging from about 4 μm to 15 μm and 90 volume-% of the particles ($D_{90}$) ranging from about 14 μm to 30 μm, to the methods for the manufacture of said crystalline particles, and to pharmaceutical compositions comprising said crystalline particles.

BACKGROUND OF THE INVENTION

U.S. Pat. No. 5,747,498 disclosed 4-(substituted phenylamino) quinazoline derivatives, processes for their preparation, pharmaceutical compositions in which they are present and method of use thereof. These compounds are Tyrosine Kinase Inhibitors and are useful in the treatment of hyperproliferative diseases, such as cancers, in mammals. Among them, erlotinib hydrochloride, chemically N-(3-ethynylphenyl)-6,7-bis(2-methoxy ethoxy)-4-quinazolinamine hydrochloride is a selective inhibitor of the erbB family of oncogenic and protooncogenic protein tyrosine kinases, such as epidermal growth factor receptor (EGFR), and is useful for the treatment of proliferative disorders, such as cancers, particularly non small cell lung cancer, pancreatic cancer, ovarian cancer, breast cancer, glioma, head cancer or neck cancer. Erlotinib is represented by the following structure:

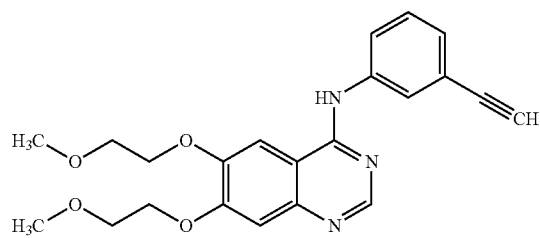 [SMILES: C#Cc1cccc(Nc2ncnc3cc(OCCOC)c(OCCOC)cc23)c1]

Polymorphism is defined as "the ability of a substance to exist as two or more crystalline phases that have different arrangement and/or conformations of the molecules in the crystal Lattice. Thus, in the strict sense, polymorphs are different crystalline forms of the same pure substance in which the molecules have different arrangements and/or different configurations of the molecules". Different polymorphs may differ in their physical properties such as melting point, solubility, X-ray diffraction patterns, etc. Polymorphic forms of a compound can be distinguished in the laboratory by analytical methods such as X-ray diffraction (XRD), Differential Scanning Calorimetry (DSC) and Infrared spectrometry (IR).

Solvent medium and mode of crystallization play very important role in obtaining a crystalline form over the other.

Erlotinib hydrochloride can exist in different polymorphic forms, which differ from each other in terms of stability, physical properties, spectral data and methods of preparation.

The U.S. Pat. No. 5,747,498 (herein after referred to as the '498 patent) makes no reference to the existence of specific polymorphic forms of erlotinib hydrochloride. In this patent, it is disclosed that the compound is isolated according to conventional techniques; more precisely, according to the embodiments exemplified, crude erlotinib hydrochloride residue (obtained by reaction of 4-chloro-6,7-bis-(2-methoxyethoxy)-quinazoline with 3-ethynylaniline or its hydrochloride salt in a solvent such as a $C_1$-$C_6$-alcohol, dimethylformamide, N-methylpyrrolidin-2-one, chloroform, acetonitrile, tetrahydrofuran, 1,4-dioxane, pyridine or other aprotic solvents, preferably isopropanol) is basified with saturated aqueous $NaHCO_3$ in the presence of methanol and chloroform followed by flash chromatography on silica using 30% acetone in hexane to afford erlotinib free base, which is further treated with hydrochloric acid in the presence of diethyl ether and chloroform to give erlotinib hydrochloride (melting point: 228°-230° C.).

PCT Patent Publication No. WO 99/55683 disclosed erlotinib mesylate anhydrate and, hydrate polymorphic forms, their method of preparation and pharmaceutical compositions containing thereof.

PCT Patent Publication No. WO 01/34574 A1 (herein after referred to as the '574 patent publication) described two crystalline forms of erlotinib hydrochloride (polymorph A and polymorph B), characterized by powder X-ray diffraction (p-XRD) pattern. The publication further taught that the synthetic procedure described and exemplified in the '498 patent produces the erlotinib hydrochloride as a mixture of the polymorphs A and B.

According to the '574 patent publication, erlotinib hydrochloride polymorph A is characterized by an X-ray powder diffraction pattern having peaks expressed as 2θ at approximately 5.58, 9.84, 11.25, 18.86, 22.70, 23.50, 24.18, 24.59, 25.40 and 29.24 degrees. As per the process exemplified in the '574 patent publication, erlotinib hydrochloride can be obtained in polymorph A form or in a mixture of polymorph A and B, by heating the filtrate containing 3-ethynylaniline in toluene, 4-chloro-6,7-bis-(2-methoxyethoxy)-quinazoline and acetonitrile to reflux temperature, cooling the reaction mass to between 19 to 25° C. over three to four hours, agitating the reaction mass at a temperature between 20 and 25° C. and isolating erlotinib hydrochloride in polymorph A form or in a mixture of polymorph A and B. The '574 patent publication further taught that the production of the polymorph A is favored by the reduction of the amount of acetonitrile relative to toluene, and particularly favored if isopropanol is used in place of acetonitrile.

According to the '574 patent publication, erlotinib hydrochloride polymorph B is characterized by an X-ray powder diffraction pattern having peaks expressed as 2θ at approximately 6.26, 12.48, 13.39, 16.96, 20.20, 21.10, 22.98, 24.46, 25.14 and 26.91 degrees. As per process described in the '574 patent publication, the erlotinib hydrochloride polymorph B can be prepared by heating to reflux alcohol, water and the erlotinib hydrochloride so as to form a solution; cooling the solution to between about 65 and 70° C.; clarifying the solution; and precipitating polymorph B by further cooling the clarified solution.

U.S. Patent Application No. 2004/0162300 A1 (hereinafter referred to as the '300 patent application) mentioned a third polymorphic form of erlotinib hydrochloride, designated as polymorph E, and characterizes it by powder X-ray diffraction, infra-red spectroscopy and by a melting point. According to the '300 patent application, erlotinib hydrochloride polymorph E (characterized by, an X-ray powder diffraction pattern having peaks expressed as 2θ at approximately 5.7, 9.7, 10.1, 11.3, 17.0, 17.4, 18.9, 19.6, 21.3, 22.8, 23.6, 24.2, 24.7, 25.4, 26.2, 26.7 and 29.3 degrees, and an IR absorption spectrum having characteristic peaks expressed in $cm^{-1}$ at approximately 3277, 3057, 16.27, 1070, 1022, 892, 873, 850, 780, 745, 725, and 652 $cm^{-1}$) can be prepared by reacting 3-ethynylaniline with 4-chloro-6,7-bis(2-methoxyethoxy)quinazoline in $(\alpha,\alpha,\alpha)$-trifluorotoluene, and precipitating erlotinib hydrochloride polymorph E from the solution of $(\alpha,\alpha,\alpha)$-trifluorotoluene.

U.S. Patent Application No. 2006/0154941 A1 described an amorphous form of erlotinib hydrochloride prepared by dissolving crystalline erlotinib hydrochloride in an alcoholic solvent to form a solution and removing the solvent from the solution by distillation or spray drying.

The processes described in the prior art produce anhydrous form of erlotinib free base, characterized by, an X-ray powder diffraction pattern having peaks expressed as 2θ at about 6.4, 12.8, 15.6, 17.2, 18.2, 19.4, 22.3, 23.4, 23.6, 25.8 and 28.3±0.2 degrees, and the Differential Scanning Calorimetry (DSC) thermogram having a sharp endotherm at 156° C.

We have discovered a novel and stable hydrated crystalline form of erlotinib free base, which differ from the anhydrous form in its stability, in its physical properties, in its spectral characteristics and in its method of preparation. The novel hydrated form is non-hygroscopic, storage stable over the time, obtainable in pure form and can be used to obtain pharmaceutically acceptable salts of erlotinib in high purity.

The erlotinib hydrochloride crystalline polymorph form A obtained by the processes described in the art, for example by the processes described and exemplified in the U.S. Pat. No. 5,747,498 and the PCT Patent Publication No. WO 01/34574 A1, is contaminated with polymorph B. Specifically, the experimental data disclosed in the '574 patent publication shows that the polymorph A has a peak in PX-RD at about 6.26±0.2 which is the characteristic peak of polymorph B.

Thus, there is a need in the art for a process for producing erlotinib hydrochloride crystalline polymorph form A substantially free of polymorph B.

Extensive laboratory and full-scale research has resulted in a new and inventive crystallization process for producing erlotinib hydrochloride crystalline polymorph form A substantially free of polymorph B which is stable over the time and has good flow properties and is suitable for formulating erlotinib hydrochloride.

The erlotinib hydrochloride product prepared by the methods as described in the prior art has a very small particle size i.e., erlotinib hydrochloride crystalline particles with a mean particle size ($D_{50}$) ranging from about 2 µm to 3.5 µm and 90 volume-% of the particles ($D_{90}$) ranging from about 4 µm to 8.5 µm resulting in similarly poor flow properties.

It is well recognized that preparation of tablets with a reproducible composition requires that all the dry ingredients have good flow properties. In cases, where the active ingredient has good flow properties, tablets can be prepared by direct compression of the ingredients. However, in many cases the particle size of the active substance is very small, the active substance is cohesive or has poor flow properties.

Thus, there is a need in the art for erlotinib hydrochloride with a desirable particle size distribution, which has good flow properties, and better dissolution and solubility properties.

Extensive laboratory and full-scale research has resulted in a new and inventive crystallization process for producing erlotinib hydrochloride crystalline particles having mean particle size ($D_{50}$) ranging from about 4 µm to 15 µm and 90 volume-% of the particles ($D_{90}$) ranging from about 14 µm to 30 µm. Said particles are useful for the manufacture of directly compressed tablets. Accurate dosing in capsules may also be with such particles.

One object of the present invention is to provide a novel and stable hydrated, crystalline form of erlotinib free base and a process for preparing it.

According to another object of the present invention is to provide a novel process for preparing erlotinib hydrochloride crystalline polymorph form A substantially free of polymorph B.

According to another object of the present invention is to provide erlotinib hydrochloride crystalline polymorph form A characterized by peaks in the powder X-ray diffraction pattern having 2θ angle positions at about 5.75, 9.88, 11.40, 18.97, 22.84, 23.65, 24.29, 24.75, 25.56 and 29.37±0.2 degrees and by the absence of a peak at about 6.26±0.2 degrees.

According to another object of the present invention is to provide a pharmaceutical composition comprising erlotinib hydrochloride crystalline polymorph form A characterized by peaks in the powder X-ray diffraction pattern having 2θ angle positions at about 5.75, 9.88, 11.40, 18.97, 22.84, 23.65, 24.29, 24.75, 25.56 and 29.37±0.2 degrees by the absence of a peak at about 6.26±0.2 degrees.

According to another object of the present invention is to provide erlotinib hydrochloride and formulations containing erlotinib hydrochloride particles having mean particle size ($D_{50}$) ranging from about 4 µm to 15 µm and 90 volume-% of the particles ($D_{90}$) ranging from about 14 µm to 30 µm, and methods for manufacturing such particles.

DETAILED DESCRIPTION OF THE INVENTION

According to one aspect of the present invention, there is provided a novel hydrated crystalline form of erlotinib free base having water content in the range of about 1-10% by weight, characterized by peaks in the powder X-ray diffraction pattern having 2θ angle positions at about 6.4, 7.4, 11.2, 12.8, 14.5, 16.3, 18.2, 20.0, 20.5, 21.9, 22.3, 23.3, 23.5, 24.6, 27.6 and 30.0±0.2 degrees. The typical X-ray powder diffraction pattern is shown in.

According to another aspect of the present invention, the crystalline erlotinib hydrate is further characterized by a Differential Scanning calorimetry (DSC) thermogram having a small endotherm in the range between 100-112° C. followed by a sharp endotherm in the range between 156-159° C. The typical DSC thermogram is shown in.

According to another aspect of the present invention, a process is provided for preparation of crystalline erlotinib hydrate having water content in the range of about 1-10% by weight, which comprises:
  a) slurrying erlotinib free base in water; and
  b) collecting the crystalline erlotinib hydrate having water content in the range of about 1-10% by weight from the slurry.

The temperature at which slurrying is done in step (a) is not critical and the slurrying is preferably carried out at a temperature below 60° C., more preferably carried out at a temperature between 0° C. and 45° C. and still more preferably carried out at 20-40° C.

The slurry obtained in step (a) is preferably stirred at least for about 30 minutes, more preferably stirred at least for about 1 hour and still more preferably stirred for about 1 hour to 4 hours.

The crystalline erlotinib hydrate in step (b) is collected from the slurry by conventional methods such as filtration or centrifugation.

According to another aspect of the present invention, another process is provided for preparation of crystalline erlotinib hydrate having water content in the range of about 1-10% by weight, which comprises:

a) dissolving erlotinib free base in an organic solvent or a mixture of organic solvents;

b) adding water as an anti-solvent to the solution obtained in step (a); and c) collecting the precipitated crystalline erlotinib hydrate having water content in the range of about 1-10% by weight.

The organic solvent used in step (a) is selected from the group consisting of acetone, tetrahydrofuran, dimethylsulfoxide, dimethylformamide, acetonitrile, and an alcoholic solvent such as methanol, ethanol, propanol, isopropyl alcohol, butanol, isoamyl alcohol. Preferable organic solvent is selected from methanol, ethanol, isopropyl alcohol and acetone.

Preferably the erlotinib free base in step (a) may be dissolved in the organic solvent at a temperature above about 30° C., more preferably at a temperature between 40° C. and reflux temperature of the solvent used and still more preferably at a temperature between 45° C. and 80° C.

Preferably water in step (b) may be added to the solution slowly at a temperature above about 30° C., more preferably at a temperature between 40° C. and reflux temperature of the solvent used and still more preferably at a temperature between 45° C. and 80° C.

The precipitated erlotinib hydrate in step (c) is collected by conventional methods such as filtration or centrifugation.

The crystalline erlotinib hydrate obtained by the processes as described above has water content in the range of about 1-10% by weight, and crystalline erlotinib hydrate shows the same characteristic powder X-ray diffraction pattern throughout this water content range.

The water content of crystalline erlotinib hydrate obtained by the processes as described above is preferably between 1.5% and 9% by weight, and more preferably between 1.8% and 8% by weight and still more preferably between 2% and 5.5% by weight.

In accordance with the present invention, the crystalline erlotinib hydrate is obtained in pure form, which is non-hygroscopic, storage stable over the time, and can be used to obtain pharmaceutically acceptable salts of erlotinib in high purity.

Erlotinib free base used as starting material may be obtained by processes described in the art, for example by the process described in the U.S. Pat. No. 5,747,498.

According to another aspect of the present invention, there is provided a process for preparing erlotinib hydrochloride crystalline polymorph form A substantially free of polymorph form B, which comprises adding hydrochloric acid to a solution of erlotinib free base in a solvent or a mixture of solvents selected from isopropyl acetate and methyl isobutyl ketone, and isolating erlotinib hydrochloride crystalline polymorph form A substantially free of polymorph B from the solution.

The erlotinib hydrochloride crystalline polymorph form A substantially free of polymorph form B obtained by the process described above is characterized by peaks in the powder X-ray diffraction pattern having 2θ angle positions at about 5.75, 9.88, 11.40, 18.97, 22.84, 23.65, 24.29, 24.75, 25.56 and 29.37±0.2 degrees. The typical X-ray powder diffraction pattern is shown in.

The term "erlotinib hydrochloride crystalline polymorph form A substantially free of polymorph form. B" refers to the erlotinib hydrochloride polymorph form A containing less than about 10% crystalline polymorph form B of erlotinib hydrochloride, preferably less than 5% crystalline polymorph form B of erlotinib hydrochloride, more preferably less than 1% crystalline polymorph form B of erlotinib hydrochloride, and still more preferably essentially free of crystalline polymorph form B of erlotinib hydrochloride. "Essentially free of crystalline polymorph form B of erlotinib hydrochloride" means that no crystalline polymorph form B of erlotinib hydrochloride can be detected within the limits of a powder X-ray diffractometer.

The preferred method of differentiating erlotinib hydrochloride crystalline polymorph form A from crystalline polymorph B is X-ray powder diffraction (PX-RD). The PX-RD pattern of erlotinib hydrochloride crystalline polymorph form A substantially free of polymorph form B, as illustrated in, contains no peak having 2θ angle position at about 6.26±0.2 degrees which peak is the characteristic peak of polymorph B.

X-ray powder diffraction provides a convenient and practical means for quantitative determination of the relative amounts of crystalline polymorph A and/or crystalline polymorph B forms in a solid mixture. X-ray powder diffraction is adaptable to quantitative applications because the intensities of the diffraction peaks of a given compound in a mixture are proportional to the fraction of the corresponding powder in the mixture. Therefore, the percent composition of crystalline polymorph A or crystalline polymorph B form of erlotinib hydrochloride in an unknown composition can be determined by using standard calibration curve, which can be constructed by spiking known amount of pure crystalline polymorph B into crystalline polymorph A of erlotinib hydrochloride to determine the percent ratio of crystalline polymorph B. For example, five or more artificial mixtures of crystalline polymorph B of erlotinib hydrochloride, at different amounts, may be prepared. Such mixtures may contain, 1%, 3%, 5%, 7%, and 10% of crystalline polymorph B of erlotinib hydrochloride. Preferably, the measurements are made on solid powder erlotinib hydrochloride. This is done by comparing the relative intensities of the peaks from the diffraction pattern of the unknown solid powder composition with a calibration curve derived from the X-ray diffraction patterns of pure known samples.

The process of the invention may be carried out by dissolving erlotinib free base in a solvent or a mixture of solvents selected from isopropyl acetate and methyl isobutyl ketone to form a clear solution; adding hydrochloric acid to the solution; and isolating erlotinib hydrochloride crystalline polymorph form A substantially free of polymorph B from the solution.

Preferably the erlotinib free base may be dissolved in the solvent or a mixture of solvents selected from isopropyl acetate and methyl isobutyl ketone at a temperature above about 30° C., more preferably at a temperature between 40° C. and reflux temperature of the solvent used and still more preferably at a temperature between 50° C. and 80° C.

Preferably hydrochloric acid may be added to the solution slowly at a temperature above about 30° C., more preferably at a temperature between 40° C. and reflux temperature of the solvent used and still more preferably at a temperature between 50° C. and 80° C.

Hydrochloric acid used may be in the form of aqueous hydrochloric acid or in the form of hydrogen chloride gas or hydrogen chloride dissolved in an organic solvent. The organic solvent used for dissolving hydrogen chloride is preferably selected from the group consisting of ethanol, methanol, isopropyl alcohol, ethyl acetate, diethyl ether, dimethyl ether and acetone. Preferably hydrogen chloride gas or hydrogen chloride dissolved in ethyl acetate may be used.

Isolation of erlotinib hydrochloride crystalline polymorph form A substantially free of polymorph B from the solution may be carried out by methods usually known in the art such as cooling, partial removal of the solvent from the solution, addition of precipitating solvent or a combination thereof.

Erlotinib free base in anhydrous form or in hydrated form may be used to prepare erlotinib hydrochloride crystalline polymorph form A substantially free of polymorph B.

According to another aspect of the present invention, there is provided erlotinib hydrochloride crystalline polymorph form A characterized by peaks in the powder X-ray diffraction pattern having 2θ angle positions at about 5.75, 9.88, 11.40, 18.97, 22.84, 23.65, 24.29, 24.75, 25.56 and 29.37±0.2 degrees and by the absence of a peak at about 6.26±0.2 degrees.

According to another aspect of the present invention, there is provided crystalline particles of erlotinib hydrochloride having mean particle size ($D_{50}$) ranging from about 4 μm to 15 μm and 90 volume-% of the particles ($D_{90}$) ranging from about 14 μm to 30 μm.

According to another aspect of the present invention, a process is provided for preparation of erlotinib hydrochloride crystalline particles having mean particle size ($D_{50}$) ranging from about 4 μm to 15 μm and 90 volume-% of the particles ($D_{90}$) ranging from about 14 μm to 30 μm, which comprises adding hydrochloric acid to a solution of erlotinib free base in isopropyl acetate, and isolating erlotinib hydrochloride crystalline particles having mean particle size ($D_{50}$) ranging from about 4 μm to 15 μm and 90 volume-% of the particles ($D_{90}$) ranging from about 14 μm to 30 μm.

The process of the invention may also be carried out by dissolving erlotinib free base in isopropyl acetate to form a clear solution; adding hydrochloric acid to the solution; and isolating erlotinib hydrochloride crystalline particles having mean particle size ($D_{50}$) ranging from about 4 μm to 15 μm and 90 volume-% of the particles ($D_{90}$) ranging from about 14 μm to 30 μm from the solution.

Preferably erlotinib hydrochloride crystalline particles obtained by the processes described above having mean particle size ($D_{50}$) ranging from about 4.5 μm to 10 μm and 90 volume-% of the particles ($D_{90}$) ranging from about 14.5 μm to 26 μm; more preferably having mean particle size ($D_{50}$) ranging from about 4.6 μm to 9.5 μm and 90 volume-% of the particles ($D_{90}$) ranging from about 14.6 μm to 24.5 μm; and still more preferably having mean particle size ($D_{50}$) ranging from about 4.8 μm to 10 μm and 90 volume-% of the particles ($D_{90}$) ranging from about 14.8 μm to 22 μm.

Preferably the erlotinib free base may be dissolved in isopropyl acetate at a temperature above about 30° C., more preferably at a temperature between 40° C. and reflux temperature of the solvent used and still more preferably at a temperature between 50° C. and 80° C.

Preferably hydrochloric acid may be added to the solution slowly at a temperature above about 30° C., more preferably at a temperature between 40° C. and reflux temperature of the solvent used and still more preferably at a temperature between 50° C. and 80° C.

Hydrochloric acid used may be in the form of aqueous hydrochloric acid or in the form of hydrogen chloride gas or hydrogen chloride dissolved in an organic solvent. The organic solvent used for dissolving hydrogen chloride is preferably selected from the group consisting of ethanol, methanol, isopropyl alcohol, ethyl acetate, diethyl ether, dimethyl ether and acetone. Preferably hydrogen chloride gas or hydrogen chloride dissolved in ethyl acetate may be used.

Isolation of erlotinib hydrochloride crystalline particles having mean particle size ($D_{50}$) ranging from about 4 μm to 15 μm and 90 volume-% of the particles ($D_{90}$) ranging from about 14 μm to 30 μm from the solution may be carried out by methods usually known in the art such as cooling, partial removal of the solvent from the solution, addition of precipitating solvent or a combination thereof.

Erlotinib free base in anhydrous form or in hydrated form may be used to prepare erlotinib hydrochloride crystalline particles having mean particle size ($D_{50}$) ranging from about 4 μm to 15 μm and 90 volume-% of the particles ($D_{90}$) ranging from about 14 μm to 30 μm.

Anhydrous erlotinib free base used as starting material may be obtained by processes described in the art, for example by the process described in the U.S. Pat. No. 5,747,498.

Hydrated form of erlotinib free base used as starting material can be obtained by the process described in the present invention.

Unless otherwise indicated, the following definitions are set forth to illustrate and define the meaning and scope of the various terms used to describe the invention herein.

The term "μm" refers to "micrometer" which is $1 \times 10^{-6}$ meter.

The term "crystalline particles" means any combination of single crystals, aggregates and agglomerates.

The term "Particle Size Distribution (P.S.D.)" means the cumulative volume size distribution of equivalent spherical diameters as determined by laser diffraction at 1 bar dispersive pressure in a Sympatec Helos equipment. "Mean particle size distribution, i.e., d(0.5)" correspondingly, means the median of said particle size distribution.

According to another aspect of the present invention there is provided a pharmaceutical composition comprising erlotinib hydrochloride crystalline polymorph form A characterized by peaks in the powder X-ray diffraction pattern having 2θ angle positions at about 5.75, 9.88, 11.40, 18.97, 22.84, 23.65, 24.29, 24.75, 25.56 and 29.37±0.2 degrees by the absence of a peak at about 6.26±0.2 degrees, and one or more pharmaceutically inert excipients.

Preferable pharmaceutical composition of erlotinib hydrochloride crystalline polymorph form A characterized by peaks in the powder X-ray diffraction pattern having 2θ angle positions at about 5.75, 9.88, 11.40, 18.97, 22.84, 23.65, 24.29, 24.75, 25.56 and 29.37±0.2 degrees and by the absence of a peak at about 6.26±0.2 degrees is selected from a solid dosage form and a oral suspension.

According to another aspect of the present invention there is provided a pharmaceutical composition comprising erlotinib hydrochloride crystalline particles having mean particle size ($D_{50}$) ranging from about 4 μm to 15 μm and 90 volume-% of the particles ($D_{90}$) ranging from about 14 μm to 30 μm, and one or more pharmaceutically inert excipients.

Preferable pharmaceutical composition of erlotinib hydrochloride crystalline particles having mean particle size ($D_{50}$) ranging from about 4 μm to 15 μm and 90 volume-% of the particles ($D_{90}$) ranging from about 14 µm to 30 µm is selected from a solid dosage form and a oral suspension.

The term "solid dosage form" as used herein includes conventional solid dosage forms such as tablet, capsule, granules, sachet, and the like.

Pharmaceutically inert excipients include all physiologically inert excipients used in the pharmaceutical art of dispensing. Examples include binders, diluents, surfactants, disintegrants, lubricants/glidants, coloring agents, and the like.

Specific examples of binders include methyl cellulose, hydroxypropyl cellulose, hydroxypropyl methylcellulose, polyvinylpyrrolidone, gelatin, gum arabic, ethyl cellulose, polyvinyl alcohol, pullulan, pregelatinized starch, agar, tragacanth, sodium alginate, propylene glycol, and the like.

Specific examples of diluents include calcium carbonate, calcium phosphate-dibasic, calcium phosphate-tribasic, calcium sulfate, microcrystalline cellulose, cellulose powdered, dextrates, dextrins, dextrose excipients, fructose, kaolin, lactitol, lactose, mannitol, sorbitol, starch, starch pregelatinized, sucrose, sugar compressible, sugar confectioners, and the like and mixtures thereof.

Surfactants include both non-ionic and ionic (cationic, anionic and zwitterionic) surfactants suitable for use in pharmaceutical dosage forms. These include polyethoxylated fatty acids and its derivatives, for example, polyethylene glycol 400 distearate, polyethylene glycol-20 dioleate, polyethylene glycol 4-150 mono dilaurate, and polyethylene glycol-20 glyceryl stearate; alcohol-oil transesterification products, for example, polyethylene glycol-6 corn oil; polyglycerized fatty acids, for example, polyglyceryl-6 pentaoleate; propylene glycol fatty acid esters, for example, propylene glycol monocaprylate; mono and diglycerides, for example, glyceryl ricinoleate; sterol and sterol derivatives; sorbitan fatty acid esters and its derivatives, for example, polyethylene glycol-20 sorbitan monooleate and sorbitan monolaurate; polyethylene glycol alkyl ether or phenols, for example, polyethylene glycol-20 cetyl ether and polyethylene glycol-10-100 nonyl phenol; sugar esters, for example, sucrose monopalmitate; polyoxyethylene-polyoxypropylene block copolymers known as "poloxamer"; ionic surfactants, for example, sodium caproate, sodium glycocholate, soy lecithin, sodium stearyl fumarate, propylene glycol alginate, octyl sulfosuccinate disodium, and palmitoyl carnitine; and the like and mixtures thereof.

Specific examples of disintegrants include low-substituted hydroxypropylcellulose (L-HPC), sodium starch glycollate, carboxymethyl cellulose, calcium carboxymethyl cellulose, sodium carboxymethyl cellulose, croscarmellose sodium A-type (Ac-di-sol), starch, crystalline cellulose, hydroxypropyl starch, pregelatinized starch, and the like and mixtures thereof.

Specific examples of lubricants/glidants include colloidal silicon dioxide, stearic acid, magnesium stearate, calcium stearate, talc, hydrogenated castor oil, sucrose esters of fatty acid, microcrystalline wax, yellow beeswax, white beeswax, and the like and mixtures thereof.

Coloring agents include any FDA approved colors for oral use.

Figure 1:
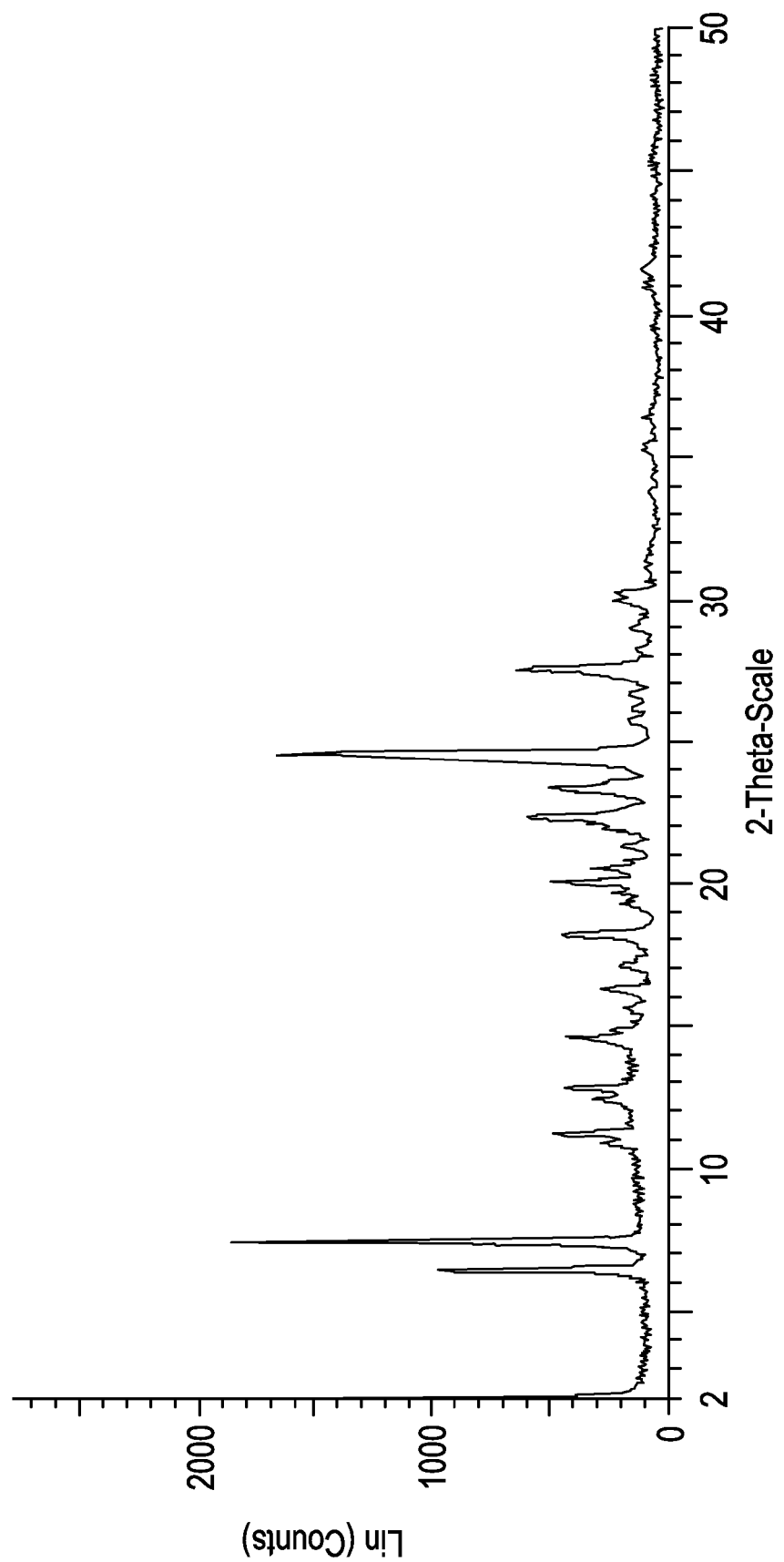
FIG. 1 shows a typical x-ray powder diffraction spectrum of hydrate form of erlotinib free base.
Figure 2:
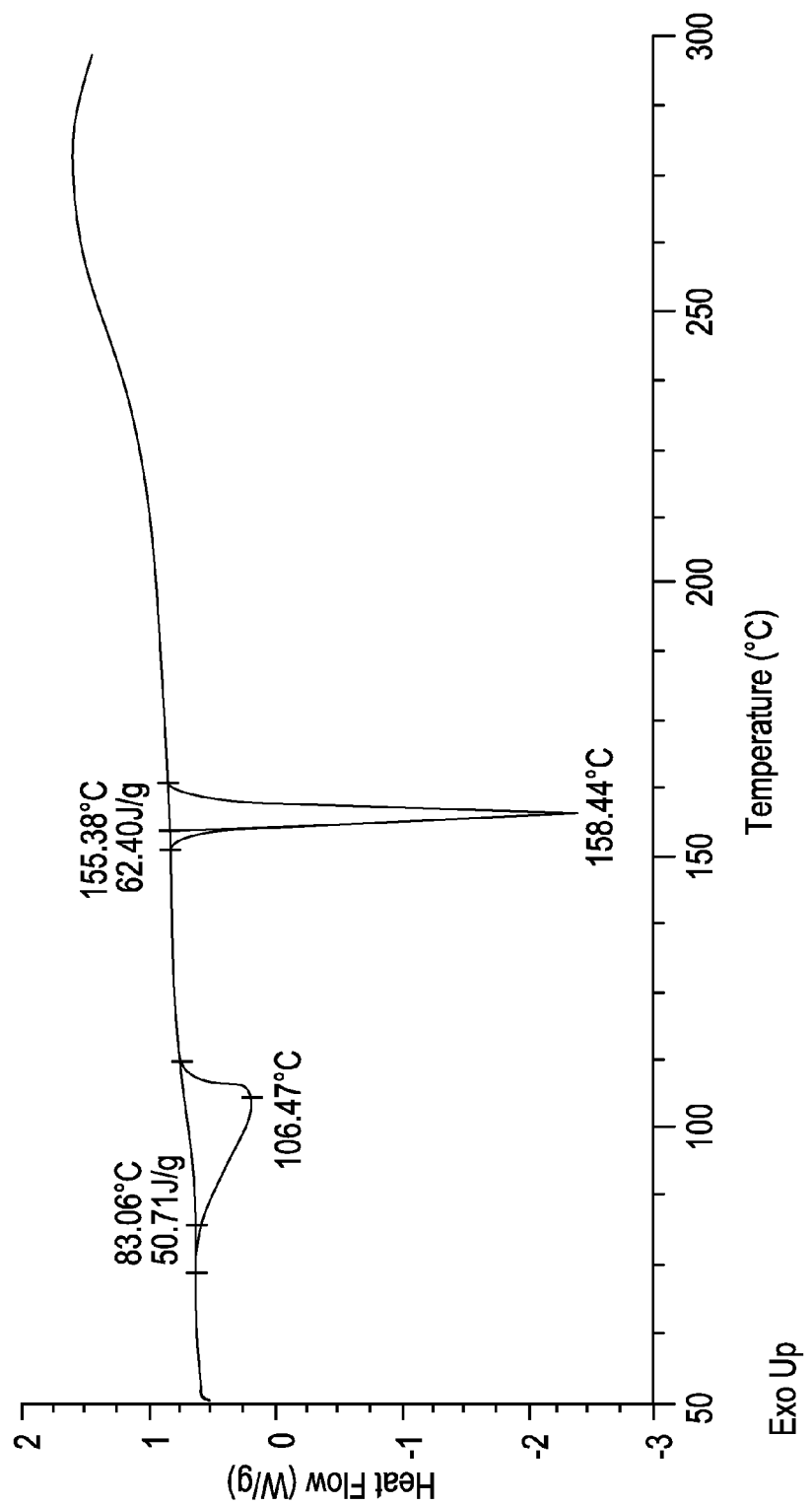
FIG. 2 shows a Differential Scanning calorimetry (DSC) thermogram of hydrate form of erlotinib free base.
Figure 3:
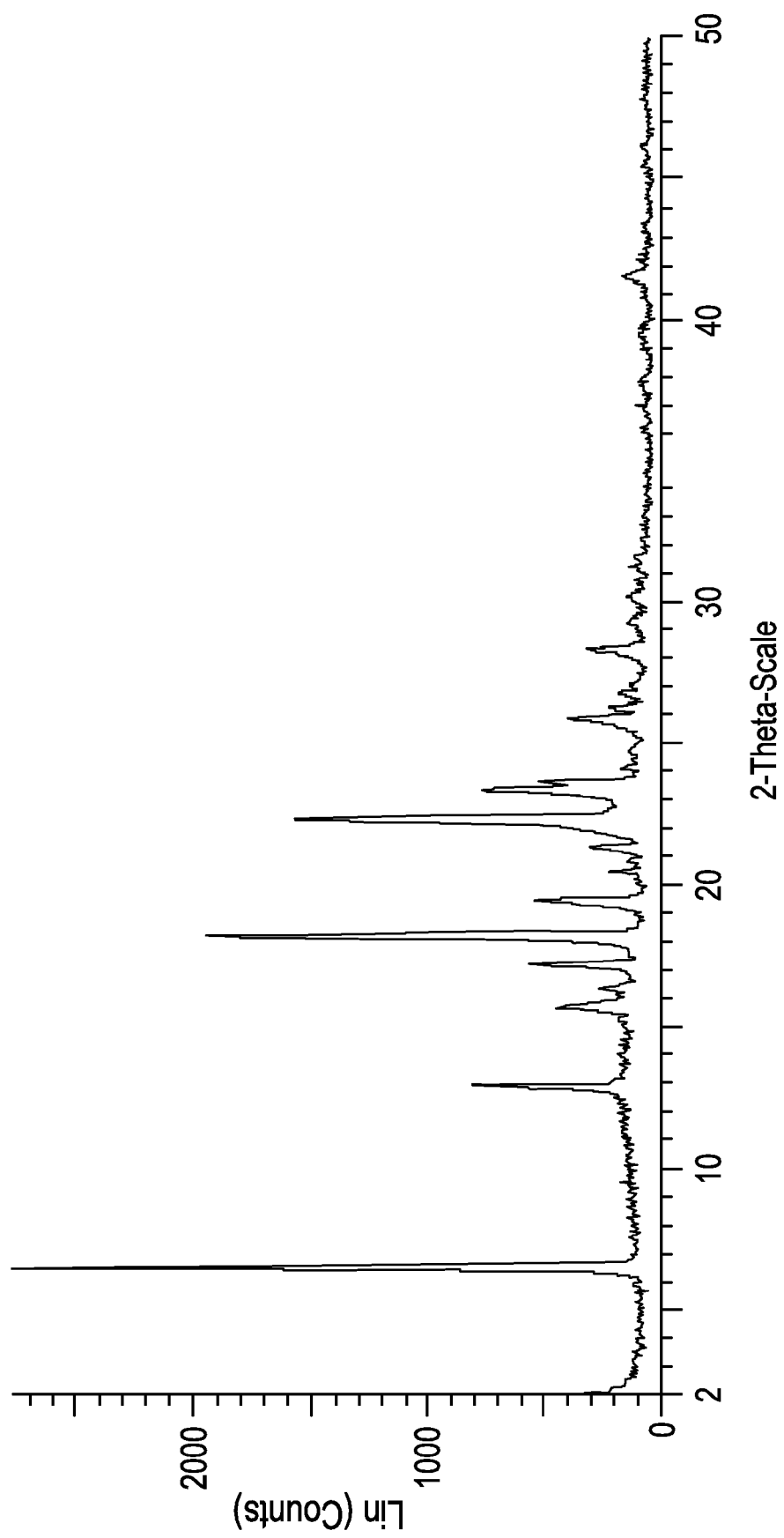
FIG. 3 shows a typical x-ray powder diffraction spectrum of anhydrous erlotinib free base.
Figure 4:
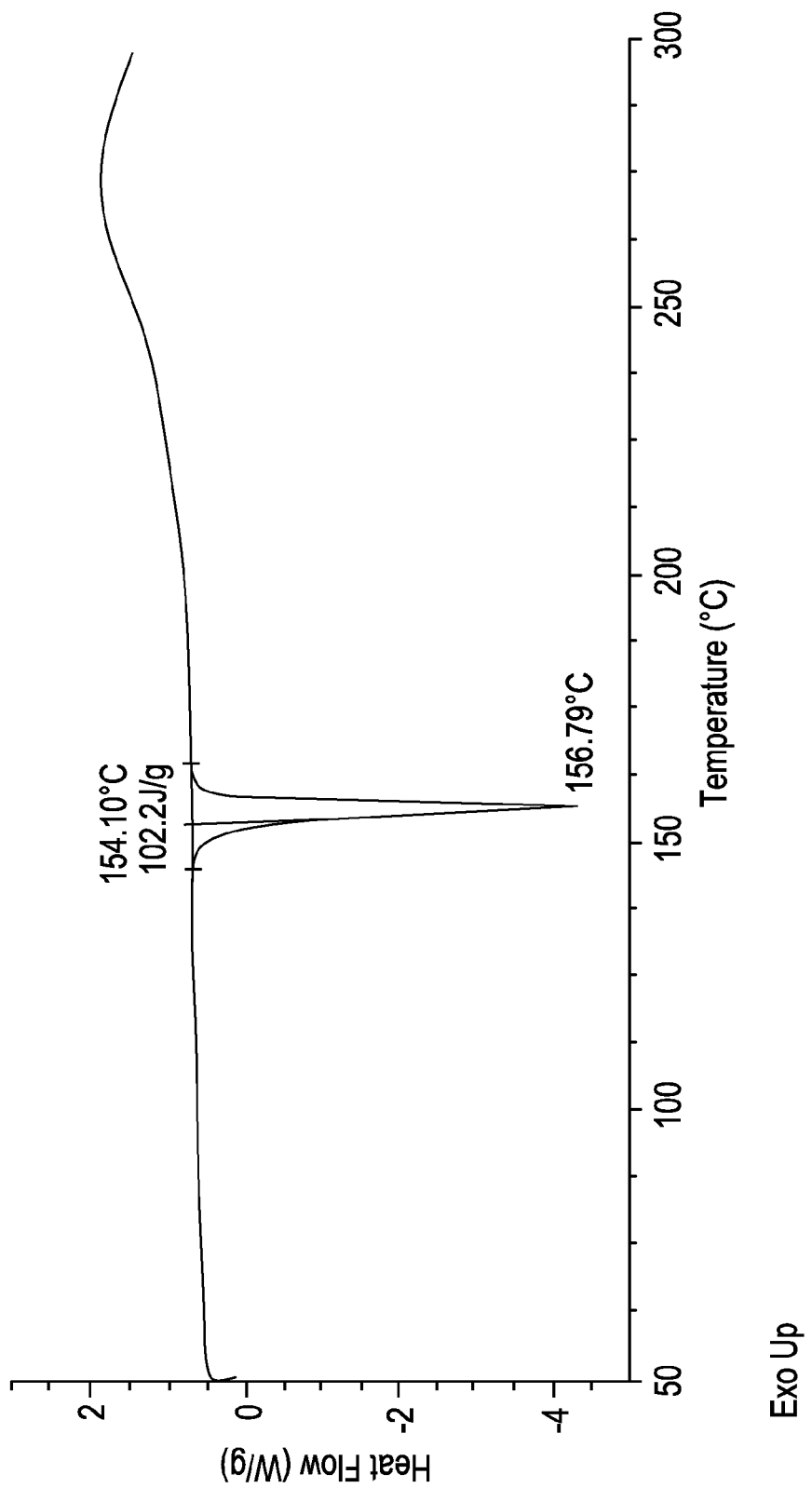
FIG. 4 shows a Differential Scanning calorimetry (DSC) thermogram of anhydrous erlotinib free base.
Figure 5:
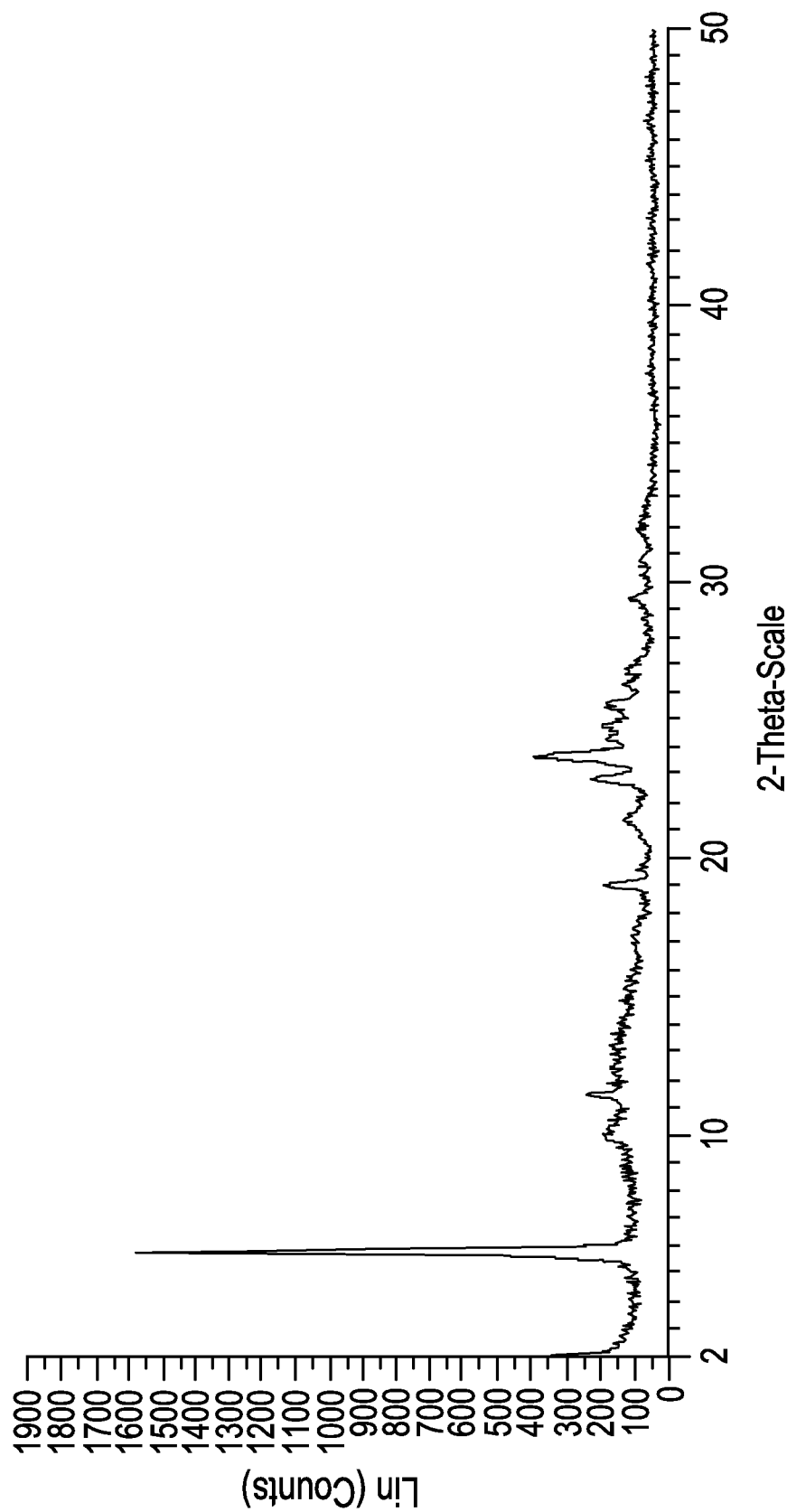
FIG. 5 shows a typical x-ray powder diffraction spectrum of erlotinib hydrochloride polymorph form A substantially free of polymorph form B.

X-ray powder diffraction spectrum was measured on a bruker axs D8 advance X-ray powder diffractometer having a copper-$k_\alpha$ radiation. Approximately 1 gm of sample was gently flattened on a sample holder and scanned from 2 to 50 degrees two-theta, at 0.03 degrees two-theta per step and a step time of 0.5 seconds. The sample was simply placed on the sample holder. The sample was rotated at 30 rpm at a voltage 40 KV and 35 mA.

DSC (Differential Scanning calorimetry) measurements were performed with a DSC Q10 (TA Instruments, Inc.). About 3 mg of the powder was placed in an open aluminum pan and it is crimped with an aluminum lid. The crimped sample is then placed in the DSC cell opposite to empty aluminum pan (as reference) and the sample was scanned at 10° C./min from 50° C. to 250° C.

The following examples are given for the purpose of illustrating the present invention and should not be considered as limitation on the scope or spirit of the invention.

REFERENCE EXAMPLES

Reference Example 1

4-Chloro-6,7-bis-(2-methoxyethoxy)-quinazoline (63 gm) and isopropyl alcohol (990 ml) are added to 3-ethynylaniline (23.6 gm) at 25-30° C. under stirring, the contents are heated to reflux and then refluxed for 1 hour 30 minutes to 2 hours. The reaction mass is cooled to 25-30° C. and stirred for 30 minutes. Filtered the material, washed with chilled isopropyl alcohol (400 ml) followed by n-hexane (300 ml) and then dried the material at 50-60° C. under vacuum for 6 hours to give 75 gm of crude erlotinib hydrochloride in polymorph form A [HPLC purity: 97%; Mean particle size ($D_{50}$): 3.42 µm and 90 volume-% of the particles ($D_{90}$): 4.53 µm].

Reference Example 2

4-Chloro-6,7-bis-(2-methoxyethoxy)-quinazoline (2.5 gm) and ethanol (40 ml) are added to 3-ethynylaniline (1.25 gm) at 25-30° C. under stirring, the contents are heated to reflux and then refluxed for 1 hour 30 minutes to 2 hours. The reaction mass is cooled to 25-30° C. and stirred for 30 minutes. Filtered the material, washed with chilled isopropyl alcohol (20 ml) followed by n-hexane (20 ml) and then dried the material at 50-55° C. under vacuum to give 3.5 gm of crude erlotinib hydrochloride in polymorph form B [HPLC purity: 99.1%; Mean particle size ($D_{50}$): 2.30 µm and 90 volume-% of the particles ($D_{90}$): 7.74 µm].

Reference Example 3

Crude erlotinib hydrochloride (37 gm, obtained in reference example 1), water (370 ml) and chloroform (370 ml) are taken into a reaction flask at 25-30° C. and start stirring. The contents are heated to 5-55° C., sodium hydroxide solution is added at 50-55° C. and then stirred for 15 minutes at 50° C. (clear solution not observed). To the reaction mass added chloroform (200 ml) and methanol (60 ml) and stirred for 15 minutes at 50° C. (clear solution observed). Separated the layers at 50° C., the organic layer is washed with water (200 ml) at 50° C. and then combined the organic layers. To the organic layer added methanol (60 ml) dried over sodium sulfate and distilled the total solvent under vacuum at 50-55° C. To the residue added n-heptane (300 ml) and stirred for 30 minutes at 25-30° C. Filtered the material, washed with n-heptane (70 ml) and then dried the material at 60-65° C. under vacuum for 3 hours 30 minutes to give 34 gm of anhydrous erlotinib free base (HPLC Purity: 98.2%, Moisture Content: 0.2%).

Reference Example 4

Crude erlotinib hydrochloride (100 gm, obtained in reference example 1), water (400 ml) and ethyl acetate (1600 ml) are taken into a reaction flask at 25-30° C. and start stirring. The contents are heated to 60° C., pH of the mass is adjusted to 9 to 10 by adding sodium hydroxide solution (30-40 ml) at 60-65° C. and then stirred for 30-35 minutes at 60-65° C. Separated the layers at 60-65° C., the organic layer is dried with sodium sulfate and then distilled off the solvent completely under vacuum at 50° C. The residue is cooled to 25-30° C., n-heptane (800 ml) is added and the stirred for 45 minutes to 1 hour at 25-30° C. Filtered the compound, washed with n-heptane (200 ml) and then dried at 60-65° C. to give 90 gm of anhydrous erlotinib free base (HPLC Purity: 99.1%, Moisture Content: 0.1%).

Reference Example 5

Erlotinib free base (5 gm, obtained in reference example 3) is dissolved in chloroform (200 ml) at 25-30° C. to form a clear solution and then added diethyl ether (50 ml). To the resulting solution slowly added 15% diethyl ether HCl (5 ml) at 25-30° C. and stirred for 30 minutes at 25-30° C. Filtered the material, washed with a mixture of diethyl ether (10 ml) and chloroform (10 ml), and then dried at 60-65° C. under vacuum to give 4.9 gm of erlotinib hydrochloride polymorph form A [HPLC purity: 99.7%; Mean particle size ($D_{50}$): 3.50 µm and 90 volume-% of the particles ($D_{90}$): 4.61 µm].

EXAMPLES

Example 1

Anhydrous erlotinib free base (33 gm, moisture content: 0.1%) is suspended in water (200 ml) at 25-30° C. (clear solution is not observed) and then stirred for 2 hours at 25-30° C. Filtered the material, washed with water (150 ml) and then dried the material at 50-55° C. to give 32 gm of crystalline erlotinib hydrate (HPLC Purity: 99.3%, Moisture Content: 4.23%).

Example 2

Anhydrous erlotinib free base (100 gm, moisture content: 0.2%) is added to methanol at 25-30° C., the contents are heated to 50-55° C. to form a clear solution and then stirred for 30 minutes at 50-55° C. To the solution slowly added 1200 ml of water during 1 hour at 50-55° C., the resulting mass is slowly cooled to 25-30° C. and then stirred for 1 hour at 25-30° C. Filtered the material, washed with the mixture (1:1) of methanol and water (100 ml) and then dried the material at 60° C. to give 90 gm of crystalline erlotinib hydrate (HPLC Purity: 99.2%, Moisture Content: 4.39%).

Example 3

Crystalline erlotinib hydrate (10 gm, Moisture Content: 4.23%) is added to isoamyl alcohol (300 ml) under stirring at 25-30° C., heated to 80° C. to form a clear solution and stirred for 30 minutes at 78-80° C. The solution is slowly cooled to 25-30° C. and then stirred for 30 minutes. Filtered the material, washed with isoamyl alcohol (20 ml) and then dried to give 9 gm of erlotinib hydrate (HPLC Purity: 99.4%, Moisture Content: 4.03%).

Example 4

Crystalline erlotinib hydrate (50 gm, Moisture Content: 4.23%) is added to methanol (250 ml) under stirring at 25-30° C. and heated to reflux to form a 0.20 clear solution. To the solution added activated carbon (4.5 gm) and stirred for 20 minutes at reflux. Filtered the mass through hyflo bed, washed the bed with hot methanol (80 ml), the filtrate is slowly cooled to 25-30° C. and then stirred for 0.1 hour at 25-30° C. Filtered the material, washed with chilled methanol (50 ml) and then dried to give 43 gm of erlotinib hydrate (HPLC Purity: 99.3%, Moisture Content: 3.98%).

Example 5

Erlotinib free base (10 gm) is added to methyl isobutyl ketone (300 ml) under stirring at 25-30° C., the contents are heated to 60° C. and then stirred at 60-65° C. to form a clear solution. To the solution slowly added 7% ethyl acetate HCl (40 ml) at 60-65° C., the resulting mass is slowly cooled to 25-30° C. and then stirred for 1 hour. Filtered the mass, washed with methyl isobutyl ketone (20 ml) and then dried at 50-55° C. to give 9.8 gm of erlotinib hydrochloride crystalline polymorph form A having polymorph form B undetected (HPLC Purity: 99.87%, Moisture Content: 0.2%).

Example 6

Erlotinib free base (10 gm) is added to isopropyl acetate (400 ml) under stirring at 25-30° C., the contents are heated to 60° C. and then stirred at 60-65° C. to form a clear solution. To the solution slowly added 7% ethyl acetate HCl (40 ml) at 60-65° C. and stirred for 2 hours at 60-65° C. The resulting mass is slowly cooled to 25-30° C. and then stirred for 1 hour. Filtered the mass, washed with the mixture of isopropyl acetate (40 ml) and ethyl acetate (4 ml) and then dried at 50-55° C. to give 9.9 gm of erlotinib hydrochloride crystalline polymorph form A having polymorph form B undetected [HPLC Purity: 99.89%; to Moisture Content: 0.15%; Mean particle size ($D_{50}$): 5.48 µm and 90 volume-% of the particles ($D_{90}$): 18.96 µm].

We claim:
1. A process for preparation of crystalline erlotinib hydrate having a water content in the range of about 1-10% by weight and characterized by peaks in the powder X-ray diffraction pattern having 2θ angle positions at about 6.4, 7.4, 11.2, 12.8, 14.5, 16.3, 18.2, 20.0, 20.5, 21.9, 22.3, 23.3, 23.5, 24.6, 27.6, 30.0+/−0.2 degrees comprising:
   a) dissolving erlotinib free base in an organic solvent or a mixture of organic solvents at a temperature between 40° C. and a reflux temperature of the solvent used to form a solution;
   b) adding water as an anti-solvent to the solution obtained in step (a); and
   c) collecting precipitated crystalline erlotinib hydrate having water content in the range of about 1-10% by weight.
2. The process as claimed in claim 1, wherein the organic solvent used in step (a) is selected from the group consisting of acetone, tetrahydrofuran, dimethylsulfoxide, dimethylfor- mamide, acetonitrile, methanol, ethanol, propanol, isopropyl alcohol, butanol, and isoamyl alcohol.

3. The process as claimed in claim 2, wherein the organic solvent is selected from the group consisting of methanol, ethanol, isopropyl alcohol and acetone.

4. The process as claimed in claim 1, wherein the precipitated erlotinib hydrate in step (c) is collected by filtration or centrifugation.

5. The process as claimed in claim 1, wherein the water content of crystalline erlotinib hydrate obtained is between 1.5% and 9% by weight.

6. The process as claimed in claim 5, wherein the water content of crystalline erlotinib hydrate is between 1.8% and 8% by weight.

7. The process as claimed in claim 6, wherein the water content of crystalline erlotinib hydrate is between 2% and 5.5% by weight.

* * * * *

UNITED STATES PATENT AND TRADEMARK OFFICE
CERTIFICATE OF CORRECTION

Page 1 of 1

PATENT NO. : 8,471,012 B2
APPLICATION NO. : 13/221986
DATED : June 25, 2013
INVENTOR(S) : Bandi Parthasaradhi Reddy et al.

It is certified that error appears in the above-identified patent and that said Letters Patent is hereby corrected as shown below:

On the title page, Item (30) in the Foreign Priority section, please ADD:

PCT/IN07/00351    Aug. 17, 2007

Signed and Sealed this
Twenty-second Day of April, 2014

Michelle K. Lee
*Deputy Director of the United States Patent and Trademark Office*